(12) United States Patent
Ikeda

(10) Patent No.: US 9,833,179 B2
(45) Date of Patent: Dec. 5, 2017

(54) BLOOD COMPONENT ANALYZING METHOD AND BLOOD COMPONENT ANALYZING APPARATUS

(71) Applicant: SEIKO EPSON CORPORATION, Tokyo (JP)

(72) Inventor: Akira Ikeda, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 405 days.

(21) Appl. No.: 14/582,619

(22) Filed: Dec. 24, 2014

(65) Prior Publication Data
US 2015/0182150 A1 Jul. 2, 2015

(30) Foreign Application Priority Data
Dec. 27, 2013 (JP) .................................. 2013-272215

(51) Int. Cl.
*A61B 5/1455* (2006.01)
*G01N 21/00* (2006.01)
(Continued)

(52) U.S. Cl.
CPC ............ *A61B 5/1455* (2013.01); *A61B 5/489* (2013.01); *G01N 21/00* (2013.01); *A61B 5/14532* (2013.01); *A61B 5/681* (2013.01)

(58) Field of Classification Search
CPC ... A61B 5/0059; A61B 5/0205; A61B 5/1455; A61B 5/14551; A61B 5/14552;
(Continued)

(56) References Cited

U.S. PATENT DOCUMENTS 6,061,583 A * 5/2000 Ishihara ............. A61B 5/14535
600/322
8,185,177 B2 5/2012 Numada et al.
(Continued)

FOREIGN PATENT DOCUMENTS

EP 1371323 A1 12/2003
EP 2347708 A1 7/2011
(Continued)

OTHER PUBLICATIONS

The Extended European Search Report for the corresponding European Application No. 14200289.8 dated Aug. 18, 2015.

*Primary Examiner* — Eric Winakur
*Assistant Examiner* — Chu Chuan (J J) Liu
(74) *Attorney, Agent, or Firm* — Global IP Counselors, LLP

(57) ABSTRACT

A blood component is accurately analyzed by appropriately extracting a blood-vessel transmitted light component. In a blood component analyzing apparatus, a sensor section has a light-emitting section that irradiates light from a predetermined irradiation position situated over a blood vessel and a light-receiving section including a first photodetector that receives light at a first light-receiving position that is different from the irradiation position and is situated over the blood vessel and a second photodetector that receives light at a second light-receiving position that is not situated over the blood vessel. A spectrum synthesizing section synthesizes a first light-reception result at the first light-receiving position and a second light-reception result at the second light-receiving position by performing a predetermined synthesis process based on a positional relationship among the irradiation position, first light-receiving position, and second light-receiving position. A blood component analyzing section analyzes a blood component using the synthesis result.

14 Claims, 11 Drawing Sheets

(51) Int. Cl.
*A61B 5/145* (2006.01)
*A61B 5/00* (2006.01)

(58) Field of Classification Search
CPC ... A61B 5/14553; A61B 5/72; A61B 5/14532; A61B 5/489; A61B 5/681
See application file for complete search history.

(56) References Cited

U.S. PATENT DOCUMENTS

| | | |
|---|---|---|
| 8,494,605 B2 | 7/2013 | Ohnishi et al. |
| 2006/0129038 A1* | 6/2006 | Zelenchuk ......... A61B 5/14535 600/322 |
| 2007/0085995 A1 | 4/2007 | Pesach et al. |

FOREIGN PATENT DOCUMENTS

| | | |
|---|---|---|
| JP | 2007-518443 A | 7/2007 |
| JP | 2008-086449 A | 4/2008 |
| JP | 2009-189389 A | 8/2009 |

\* cited by examiner

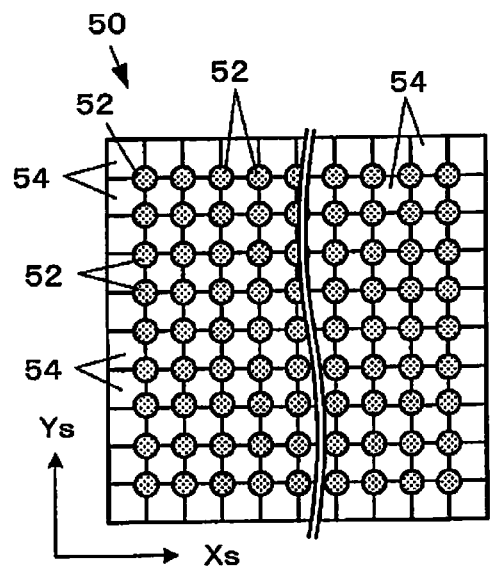
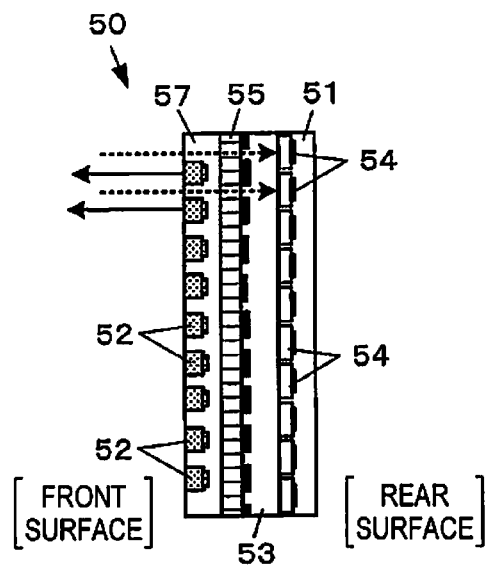
FIG. 2A    FIG. 2B
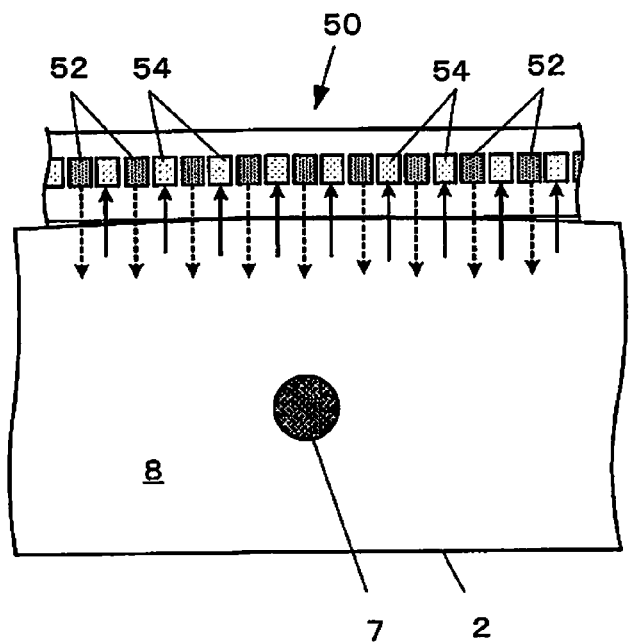
FIG. 3

| DIAMETER OF BLOOD VESSEL \ DEPTH OF BLOOD VESSEL | $V_{11} \sim V_{12}$ | $V_{12} \sim V_{13}$ | ... |
|---|---|---|---|
| $V_{21} \sim V_{22}$ | $D_{11}(R1, Fy(R1), Fx(R1))$ | $D_{21}(R1, Fy(R1), Fx(R1))$ | ... |
| $V_{22} \sim V_{23}$ | $D_{12}(R1, Fy(R1), Fx(R1))$ | $D_{22}(R1, Fy(R1), Fx(R1))$ | ... |
| ⋮ | ⋮ | ⋮ | ⋱ |

FIG.15

BLOOD COMPONENT ANALYZING METHOD AND BLOOD COMPONENT ANALYZING APPARATUS

PRIORITY INFORMATION

The present invention claims priority to Japanese Patent Application No. 2013-272215 filed Dec. 27, 2013, which is incorporated herein by reference in its entirety.

BACKGROUND

1. Technical Field

The present invention relates to a blood component analyzing method and the like for analyzing a blood component.

2. Related Art

In recent years, non-invasive diagnosis that is performed by irradiating a subject with measuring light has been practiced. For example, methods for analyzing the concentration of a blood component using luminance values of a biological image that is obtained by imaging a living body are known (see JP-A-2009-189389 and JP-A-2008-86449, for example).

Incidentally, since living bodies scatter light, measuring light irradiated onto the surface of a living body is propagated through the living body while being complexly scattered therein. Moreover, body tissues that form a living body are not homogeneous, and, for example, structures, substances, and the like such as cellular tissue and interstitial fluid are present in addition to blood vessels. Accordingly, the result of receiving light at a light-receiving position contains light transmitted through and reflected by body tissues other than the blood vessels, and furthermore, light reflected by the surface of the living body and other light are added to the light-reception result. For this reason, there are cases where merely irradiating the entire region of a measurement part with the measuring light and simply measuring (capturing an image of) the received light would allow a large amount of unwanted transmitted light and reflected light to be added to the received light, resulting in a decrease in the accuracy of blood component analysis.

SUMMARY

An advantage of some aspects of the invention is to accurately analyze a blood component by appropriately extracting a blood-vessel transmitted light component.

According to a first aspect of the invention, a blood component analyzing method includes irradiating light from a predetermined irradiation position that is situated over a blood vessel, receiving light at a first light-receiving position that is different from the irradiation position and is situated over the blood vessel, receiving light at a second light-receiving position that is not situated over the blood vessel, synthesizing a first light-reception result at the first light-receiving position and a second light-reception result at the second light-receiving position by performing a predetermined synthesis process based on a positional relationship among the irradiation position, the first light-receiving position, and the second light-receiving position, and analyzing a blood component using a result of the synthesis. Note that in this specification, the positional relationship between the irradiation position of light and the blood vessel that is included in the body tissues is described such that the predetermined irradiation position "is situated over" the blood vessel. Similarly, the positional relationship between the light-receiving position and the blood vessel that is included in the body tissues is described such that the light-receiving position "is situated over" the blood vessel. "Over" as used herein does not necessarily mean a vertically upward direction, but "over" is used as a general expression of the positional relationship during usage by a user.

Moreover, a blood component analyzing apparatus may also be configured as another aspect of the invention, the apparatus including a light source that irradiates light from a predetermined irradiation position that is situated over a blood vessel, a first photodetector that receives light at a first light-receiving position that is different from the irradiation position and is situated over the blood vessel, a second photodetector that receives light at a second light-receiving position that is not situated over the blood vessel, a synthesis section that synthesizes a first light-reception result at the first light-receiving position and a second light-reception result at the second light-receiving position by performing a predetermined synthesis process based on a positional relationship among the irradiation position, the first light-receiving position, and the second light-receiving position, and an analysis section that analyzes a blood component using a result of the synthesis.

In the case where light is irradiated from over the blood vessel, the first light-reception result at the first light-receiving position, which is different from the irradiation position and is situated over the blood vessel, contains a larger amount of blood-vessel transmitted light component when compared with the second light-reception result at the second light-receiving position, which is not situated over the blood vessel. According to the first and the other aspects of the invention, it is possible to synthesize the first light-reception result and the second light-reception result by performing the predetermined synthesis process based on the positional relationship among the irradiation position, the first light-receiving position, and the second light-receiving position. Accordingly, it is possible to accurately analyze a blood component by appropriately extracting the blood-vessel transmitted light component.

A second aspect of the invention is the blood component analyzing method according to the first aspect of the invention, wherein the synthesis includes setting a first proportion of the blood-vessel transmitted light component contained in the first light-reception result and a second proportion of an amount of the blood-vessel transmitted light component contained in the second light-reception result, and performing the predetermined synthesis process using the first proportion and the second proportion.

According to the second aspect of the invention, the first light-reception result and the second light-reception result can be synthesized using the first proportion of the blood-vessel transmitted light component contained in the first light-reception result and the second proportion of the blood-vessel transmitted light component contained in the second light-reception result. Accordingly, a synthesis result that reflects the amounts of blood-vessel transmitted light component contained in the first light-reception result and the second light-reception result can be obtained.

A third aspect of the invention is the blood component analyzing method according to the second aspect of the invention, wherein performing the predetermined synthesis process includes calculating a difference between an amount (hereinafter referred to as "first amount of blood-vessel transmitted light component") of the blood-vessel transmitted light component contained in the first light-reception result, the amount being calculated using the first proportion, and an amount (hereinafter referred to as "second amount of blood-vessel transmitted light component") of the blood-vessel transmitted light component contained in the second light-reception result, the amount being calculated using the second proportion.

According to the third aspect of the invention, the difference between the first amount of blood-vessel transmitted light component contained in the first light-reception result and the second amount of blood-vessel transmitted light component contained in the second light-reception result can be obtained as the synthesis result.

A fourth aspect of the invention is the blood component analyzing method according to the second or third aspect of the invention, wherein setting the first proportion includes setting the first proportion at a proportion corresponding to a distance between the irradiation position and the first light-receiving position, and setting the second proportion includes setting the second proportion at a proportion corresponding to a distance between the irradiation position and the second light-receiving position.

According to the fourth aspect of the invention, it is possible to set the first proportion taking the distance between the irradiation position and the first light-receiving position into account and set the second proportion taking the distance between the irradiation position and the second light-receiving position into account. Accordingly, a synthesis result that reflects the amounts of blood-vessel transmitted light component contained in the first light-reception result and the second light-reception result even more can be obtained.

A fifth aspect of the invention is the blood component analyzing method according to any one of the second to fourth aspects of the invention, the method further including setting the first proportion and the second proportion to be variable according to a depth of the blood vessel.

According to the fifth aspect of the invention, the first proportion and the second proportion can be set taking the depth of the blood vessel into account. Accordingly, a synthesis result that reflects the amounts of blood-vessel transmitted light component contained in the first light-reception result and the second light-reception result even more can be obtained.

A sixth aspect of the invention is the blood component analyzing method according to any one of the second to fifth aspects of the invention, the method further including setting the first proportion and the second proportion such that, when compared with the first proportion relative to the second proportion when the blood vessel is at a first depth, the first proportion relative to the second proportion is larger when the blood vessel is at a second depth that is deeper than the first depth.

According to the sixth aspect of the invention, the first proportion and the second proportion can be set such that the first proportion relative to the second proportion when the depth of the blood vessel is deep is larger than that when the depth of the blood vessel is shallow.

A seventh aspect of the invention is the blood component analyzing method according to any one of the second to sixth aspects of the invention, the method further including setting the first proportion and the second proportion to be variable according to a diameter of the blood vessel.

According to the seventh aspect of the invention, the first proportion and the second proportion can be set taking the diameter of the blood vessel into account. Accordingly, a synthesis result that reflects the amounts of blood-vessel transmitted light component contained in the first light-reception result and the second light-reception result even more can be obtained.

An eighth aspect of the invention is the blood component analyzing method according to any one of the second to seventh aspects of the invention, the method further including setting the first proportion and the second proportion such that, when compared with the second proportion relative to the first proportion when the blood vessel has a first diameter, the second proportion relative to the first proportion is larger when the blood vessel has a second diameter that is larger than the first diameter.

According to the eighth aspect of the invention, the first proportion and the second proportion can be set such that the second proportion relative to the first proportion when the blood vessel is thick is larger than that when the blood vessel is thin.

A ninth aspect of the invention is the blood component analyzing method according to any one of the second to eights aspects of the invention, the method further including determining the first light-receiving position and the second light-receiving position by changing a distance from the irradiation position to the first light-receiving position and a distance from the irradiation position to the second light-receiving position according to a depth of the blood vessel.

According to the ninth aspect of the invention, the first light-receiving position and the second light-receiving position can be determined by changing the distance from the irradiation position to the first light-receiving position and the distance from the irradiation position to the second light-receiving position according to the depth of the blood vessel.

A tenth aspect of the invention is the blood component analyzing method according to any one of the first to ninth aspects of the invention, the method further including determining the first light-receiving position and the second light-receiving position by changing a distance from the irradiation position to the first light-receiving position and a distance from the irradiation position to the second light-receiving position according to a diameter of the blood vessel.

According to the tenth aspect of the invention, the first light-receiving position and the second light-receiving position can be determined by changing the distance from the irradiation position to the first light-receiving position and the distance from the irradiation position to the second light-receiving position according to the diameter of the blood vessel.

An eleventh aspect of the invention is the blood component analyzing method according to any one of the first to tenth aspects of the invention, wherein a direction containing the irradiation position and the first light-receiving position and a direction containing the irradiation position and the second light-receiving position intersect each other.

According to the eleventh aspect of the invention, the first light-receiving position and the second light-receiving position can be determined so as to have a positional relationship in which the direction containing the irradiation position and the first light-receiving position and the direction containing the irradiation position and the second light-receiving position intersect each other.

BRIEF DESCRIPTION OF THE DRAWINGS

The invention will be described with reference to the accompanying drawings, wherein like numbers reference like elements.

FIGS. 2A and 2B are diagrams showing a configuration example of a sensor module.

FIG. 3 is a conceptual diagram illustrating a method for acquiring blood vessel position information.

FIG. 15 shows an example of data configuration of an applied ratio data table.

DESCRIPTION OF EXEMPLARY EMBODIMENTS

The following describes an embodiment for carrying out a blood component analyzing method and a blood component analyzing apparatus of the invention with reference to the drawings. Note that the invention is not limited by the embodiment described below, and embodiments to which the invention is applicable are not limited to the embodiment below. In the following description of the drawings, like numbers reference like elements.

Figure 1:
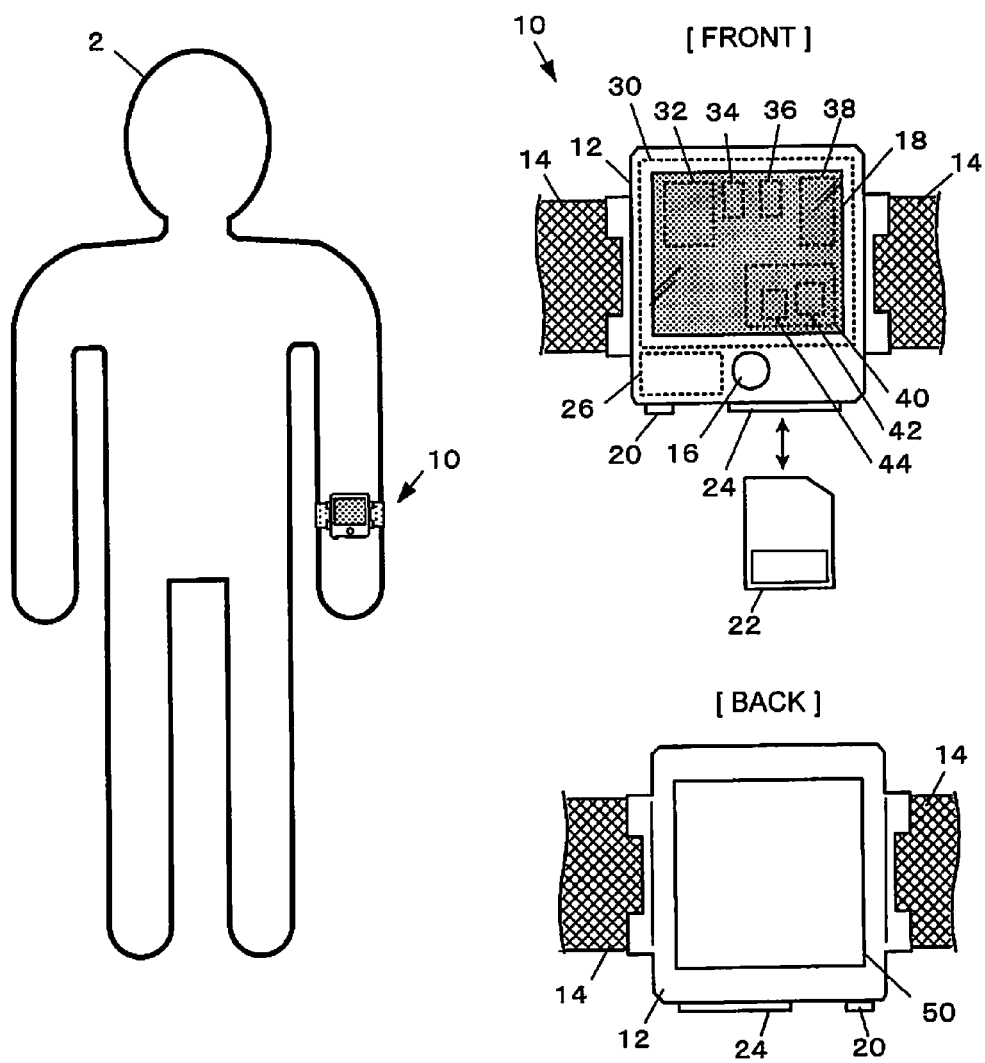
FIG. 1 shows external views showing a configuration example of a blood component analyzing apparatus.

FIG. 1 shows external views showing a configuration example of a non-invasive blood component analyzing apparatus 10 according to the present embodiment. The blood component analyzing apparatus 10 functions as an analyzer that analyzes a blood component of the blood of a subject 2 and also as a data logger that stores analysis data, and can also be regarded as a kind of computer. As shown in FIG. 1, the blood component analyzing apparatus 10 has a wristwatch-like appearance and, during usage, is put on and fixed to a body part such as an arm, a leg, or the neck of the subject 2 with a band 14 attached to a main body case 12.

The blood component analyzing apparatus 10 includes, on a surface (surface that faces outward when the apparatus is put on the subject 2) of the main body case 12, an operation switch 16 and a touch panel 18 that constitute an operation input unit, the touch panel 18 also constituting an image display unit. A user can input various operations such as an analysis starting operation by using them.

Also, a communication device 20 to which a cable for communicating with an external device can be detachably connected and a reader/writer 24 that realizes reading/writing of data from/to a memory card 22 are provided on a side surface of the main body case 12. Also, a sensor module 50 serving as a main sensor for performing irradiation with measuring light and measurement of received light is provided on a back surface (surface that comes into contact with the skin of the subject 2 when the apparatus is put on the subject 2) side of the main body case 12. Moreover, a rechargeable internal battery 26 and a control board 30 are contained in the main body case 12.

In the case where the communication device 20 is configured to perform wireless communication with an external device, the communication device 20 is realized by a wireless communication module and an antenna.

The memory card 22 is a removable, data-rewritable non-volatile memory. Although a flash memory is used in the present embodiment, other rewritable non-volatile memories such as a ferroelectric random access memory (FeRAM) and a magnetoresistive random access memory (MRAM) may also be used.

The method for charging the internal battery 26 can be set as appropriate. For example, a configuration may be adopted in which an additional electric contact is provided on the back surface side of the main body case 12, and the apparatus is placed on a cradle connected to a home power source and is energized and charged via the cradle through the electric contact, or a contactless, wireless charging method may be adopted.

The control board 30 performs integrated control of the blood component analyzing apparatus 10. Specifically, a CPU (central processing unit) 32, a main memory 34, an analysis data memory 36, a touch panel controller IC (integrated circuit) 38, and a sensor module controller 40 are mounted on the control board 30. In addition to these, electronic components such as a power management IC and an image processing IC can also be mounted as appropriate.

The main memory 34 is a storage medium that is capable of storing a program and initial setting data and storing calculation values of the CPU 32, and is realized by using a RAM, a ROM, a flash memory, and the like as appropriate. Note that a configuration may also be adopted in which the program and the initial setting data are stored in the memory card 22.

The analysis data memory 36 is a data-rewritable non-volatile memory and serves as a storage medium for storing blood component analysis data. Although a flash memory is used in the present embodiment, other rewritable non-volatile memories such as a ferroelectric random access memory (FeRAM) and a magnetoresistive random access memory (MRAM) may also be used. Note that a configuration may also be adopted in which the analysis data is stored in the memory card 22.

The touch panel controller IC 38 realizes driver functions for displaying an image on the touch panel 18 and also realizes functions for realizing touch input. Both the touch panel controller IC 38 and the touch panel 18 can be realized by using known technologies as appropriate.

The sensor module controller 40 has an IC or a circuit that performs the function of irradiating the measuring light using the sensor module 50 and the function of controlling reception of light (transmitted light and reflected light) obtained by the measuring light being transmitted through and reflected by the body tissues of the subject 2.

More specifically, the sensor module controller 40 includes a light emission controller section 42 that is constituted by an IC or a circuit that controls light emission of a plurality of light-emitting elements (elements that emit the measuring light when energized) of the sensor module 50 individually, and a light reception controller section 44 that is constituted by an IC or a circuit that controls light reception of a plurality of light-receiving elements (elements that generate electric signals corresponding to the quantity of the received light) of the sensor module 50.

Note that the sensor module controller 40 may also be configured by a plurality of ICs. For example, a configuration is also possible in which different ICs are used as the IC or the circuit corresponding to the light emission controller section 42 and the IC or the circuit corresponding to the light reception controller section 44. Alternatively, a configuration is also possible in which part of the functions of these sections is realized by the CPU 32.

FIGS. 2A and 2B show a configuration example of the sensor module 50 according to the present embodiment, and correspond to a front view and a cross-sectional view, respectively. Note that in order to facilitate understanding, the light-emitting elements 52 and the light-receiving elements 54 are intentionally shown in an enlarged manner. Also, the size, aspect ratio, and the like are not limited to those in these diagrams and can be set as appropriate.

The sensor module 50 is a device configured by stacking a layer in which the plurality of light-emitting elements 52 serving as light sources are arranged in a plane and a layer in which the plurality of light-receiving elements 54 serving as first photodetectors and second photodetectors are arranged in a plane. In other words, the sensor module 50 is an image sensor having light sources inside and is a sensor array that realizes both the functions of irradiation with measuring light and reception of light. The sensor module 50 may also be configured to be integral with the sensor module controller 40.

The light-emitting elements 52 constitute an irradiation section that irradiates measuring light, and can be realized by, for example, LEDs (light emitting diodes), OLEDs (organic light-emitting diodes), or the like. In the case where blood component analysis is performed to calculate (estimate) the concentration of glucose in the blood (so-called "blood sugar level"), elements that are capable of irradiation with light that contains near-infrared light (about 700 [nm] to 1300 [nm]) having high transmission through a living body are used. The reason for this is that near-infrared light includes a range of wavelengths that are unlikely to be scattered in a living body and are not much absorbed by water that is present in great quantity in a living body. In contrast, visible light, which is not much absorbed by water but is likely to be scattered, makes it difficult to obtain a light intensity distribution that reflects information on a deep part in a living body. Also, the wavelengths of the infrared light region and the terahertz region are much absorbed by water even though being less likely to be scattered, and thus has low transmission through a living body. The present embodiment is described assuming that the light-emitting elements 52 perform irradiation with near-infrared light, and blood sugar level is calculated as the blood component.

The light-receiving elements 54 are imaging devices that receive transmitted light and reflected light of the measuring light and output electric signals corresponding to the quantity of the received light, and can be realized by, for example, a semiconductor device such as a CCD (charge coupled device) image sensor or a CMOS (complementary metal oxide semiconductor) image sensor. It is assumed that each light-receiving element 54 includes a plurality of elements that receive R, G, and B wavelength components, respectively.

Now, the sensor module 50 includes, in sequence from the base side (front side of the main body case 12), 1) a light-receiving layer 51 in which the plurality of light-receiving elements 54 are arranged in a plane in a grid-like pattern, 2) a light-shielding layer 53 that selectively shields light other than light traveling toward the light-receiving elements 54, 3) a spectroscopic layer 55 that selectively transmits near-infrared light, and 4) a light-emitting layer 57 in which the plurality of light-emitting elements 52 are arranged in a plane in a grid-like pattern so as to be located between adjacent light-receiving elements 54 without blocking optical paths along which light transmitted through and reflected by body tissues reaches the light-receiving elements 54.

The light-receiving elements 54 of the light-receiving layer 51 are arranged, as in a known CCD image sensor or the like, in a matrix in which pixels can be specified using an Xs-Ys orthogonal coordinate system. That is to say, the sensor module 50 functions similarly to a known image sensor. Note that the shape, size, and arrangement pattern of the light-receiving elements 54 can be set as appropriate.

When the sensor module 50 is viewed from the front (back side of the main body case 12), the light-emitting elements 52 of the light-emitting layer 57 are arranged one in each portion at which corners of neighboring light-receiving elements 54 meet. More specifically, one light-emitting element 52 is arranged in each portion at which corners of four light-receiving elements 54 meet, and all of the light-emitting elements 52 are arranged in a matrix in which these light-emitting elements can be specified using the same Xs-Ys orthogonal coordinate system as the light-receiving elements 54. In the present embodiment, a drive mechanism that selectively causes the light-emitting elements 52 to emit light is provided, and drive control can be performed similarly to, for example, an active matrix scheme of liquid crystal panel displays.

To produce the sensor module 50 having the above-described layered structure, a semiconductor microfabrication technology for use in manufacturing of a known CCD image sensor or OLED display can be applied as appropriate.

Note that the size and the pitch of the light-emitting elements 52, the size and the pitch of the light-receiving elements 54, and the like can be set as appropriate. For example, the pitch is preferably set at 1 to 500 [μm], and can also be set at, for example, about 50 to 200 [μm] in view of a trade-off between the manufacturing cost and the measurement accuracy. Moreover, it is also possible to provide a light-condensing layer having additional optical elements in the sensor module 50 for the purpose of narrowing the irradiation range of or polarizing the measuring light irradiated from the light-emitting elements 52 or for the purpose of precisely collecting and directing light transmitted through and reflected by body tissues to the light-receiving elements 54. Also, a protective layer or the like that prevents damage to the surface of the sensor module 50 may be provided as appropriate. Moreover, the present invention is not limited to a configuration in which the light-emitting elements 52 and the light-receiving elements 54 are provided in layers, and the light-emitting elements 52 and the light-receiving elements 54 may also be arranged side-by-side.

Principles

The blood component analyzing apparatus 10 is fixed with the band 14 such that the back surface thereof to which the sensor module 50 is exposed is in close contact with the skin of the subject 2. Bringing the sensor module 50 into close contact with the skin makes it possible to suppress factors, such as reflection of the measuring light by the skin surface and scattering of the measuring light by tissues near the skin surface, that lower the measurement accuracy.

To perform the analysis, first, a portion of a blood vessel that is situated under the skin of a body covered by the sensor module 50 is selected as a blood vessel to be measured, and irradiation of that blood vessel with the measuring light and measurement of the received light are performed. Then, a blood-vessel transmitted light component that is transmitted through the blood vessel to be measured is extracted from the measurement result (light-reception result), a synthesis process for synthesizing a relative spectrum that reflects the amount of the blood-vessel transmitted light component is performed, and the level of blood sugar contained in the blood is calculated.

To select the blood vessel to be measured, first, it is necessary to locate a blood vessel under the skin that is covered by the sensor module 50. FIG. 3 is a conceptual diagram illustrating a method for acquiring the position of a blood vessel according to the present embodiment, and corresponds to a cross section of a portion of the subject 2 that is covered by the sensor module 50. Note that the sensor module 50 is shown in a simplified manner.

To acquire the blood vessel position, similarly to vein pattern detection of a known vein authentication technology, all of the light-emitting elements 52 provided in the sensor module 50 are caused to simultaneously emit light, thereby irradiating the entire region of a measurement part of the subject 2 with the measuring light. Then, all of the light-receiving elements 54 are used to perform received-light measurement (capturing an image) of light that is transmitted through and reflected by subcutaneous body tissues (subcutaneous tissues), thereby acquiring a biological image.

Here, the biological image that is imaged by the sensor module 50 is a collection of luminance data on pixels corresponding respectively to the light-receiving elements 54 of the sensor module 50, and is obtained as a two-dimensional image of the same Xs-Ys orthogonal coordinate system as the pixel coordinates of the sensor module 50. Blood vessels are more likely to absorb near-infrared light than body tissue portions (hereinafter referred to as "non-blood-vessel portions") other than the blood vessels, due to the effect of the blood flowing therethrough, and therefore a blood vessel portion is lower in luminance and thus darker than the non-blood-vessel portions. Accordingly, it is possible to determine with respect to each pixel whether a blood vessel is imaged or a non-blood-vessel portion is imaged, or in other words to determine whether or not a blood vessel is present under each light-receiving element 54, by extracting a low-luminance portion in the biological image.

Figure 4:
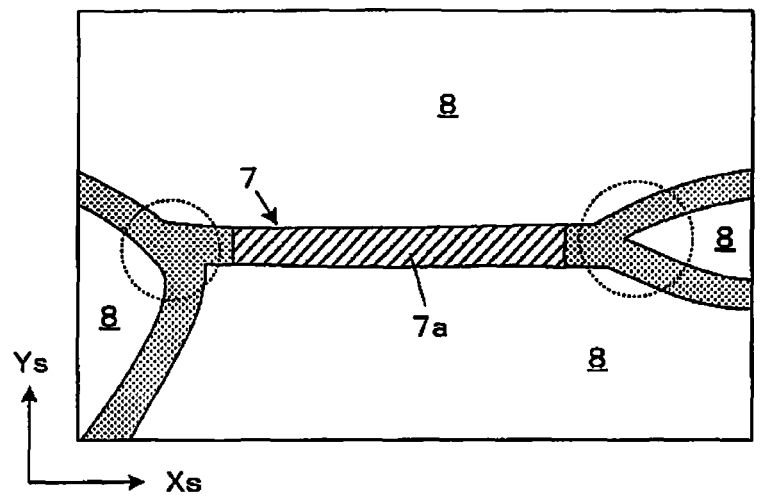
FIG. 4 schematically shows a biological image.

FIG. 4 schematically shows a biological image of a measurement part of the subject 2. In the example shown in FIG. 4, belt-shaped portions that are shaded with diagonal lines or a dot pattern indicate a blood vessel 7, and white portions indicate non-blood-vessel portions 8. Note that the method for acquiring the blood vessel position is not limited to the method exemplified above. For example, a method is also conceivable in which relative positions of inner structures of a living body are acquired beforehand by using a known biological tomographic measurement technology such as ultrasonic echo, MRI (magnetic resonance imaging), or CT (computed tomography), and the blood vessel position is determined based on the acquired relative positions.

After the position of the blood vessel 7 is acquired, a light-emitting element 52 that is situated over the blood vessel 7 is selectively used as an irradiation position, and measuring light (near-infrared light) irradiated from this irradiation position and transmitted through and reflected by the subcutaneous tissue is received and measured. More specifically, a light-emitting element 52 with respect to which the irradiation position is aligned with the structural center of the blood vessel is selectively used.

Note that transmitted light that is transmitted through the non-blood-vessel portions, for example, portions such as the cellular tissue and the interstitial fluid other than the blood vessel to be measured may have an effect on a spectroscopic spectrum of the blood-vessel transmitted light (hereinafter referred to as "blood-vessel light absorption spectrum") that is originally desired to be obtained. Also, if the measuring light is incident on any non-blood-vessel portion, not a little reflected light occurs, similarly becoming a factor having an effect on the blood-vessel light absorption spectrum. In order to suppress the effects of such unwanted transmitted light and reflected light, in actual processing, a blood vessel part that is suitable for measurement is selected as a measurement target from the blood vessel 7 that is located in the above-described manner. Specifically, a bifurcation point, a merging point, and the like of the blood vessel 7 that are enclosed by dashed lines in FIG. 4 are excluded from the measurement target. The reason for this is that if the measuring light covers such bifurcation points, merging points, and the like, transmitted light and the like of the non-blood-vessel portions is likely to be mixed in light (hereinafter referred to as "total transmitted light") that is received at a light-receiving position. Moreover, the blood vessel part to be used as the measurement target is required to have at least a certain length. For example, a blood vessel part 7a that is shaded by diagonal lines in FIG. 4 is selected as the measurement target.

Figure 5:
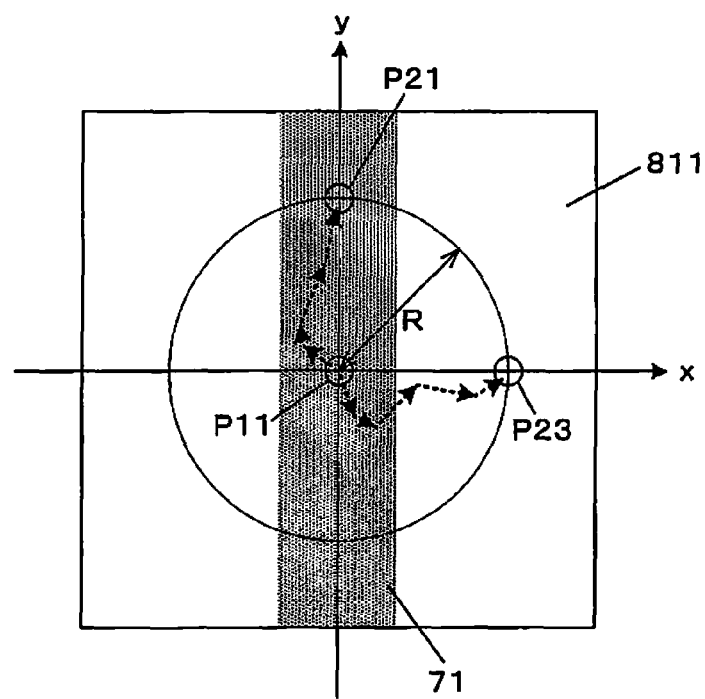
FIG. 5 is a plan view schematically showing the skin surface.
Figure 6:
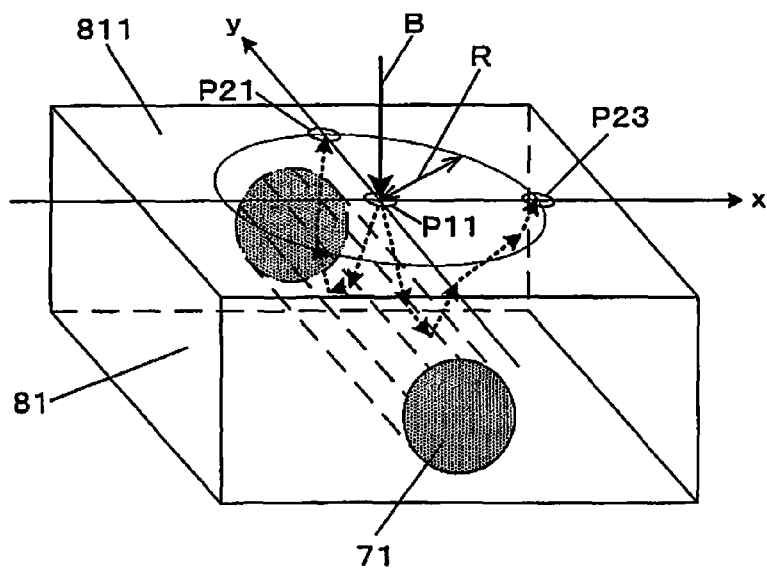
FIG. 6 is a perspective view schematically showing the subcutaneous tissue layer.

Next, the synthesis process will be described. FIG. 5 is a plan view schematically showing a skin surface (body tissue surface) 811 of a measurement part, and the position of a blood vessel 71 to be measured, which runs under the skin, is indicated by shading. Also, FIG. 6 is a perspective view schematically showing a subcutaneous tissue layer 81 under the skin surface 811 shown in FIG. 5. Here, as shown in FIGS. 5 and 6, in a plane that is parallel to the skin surface 811, a coordinate system in which the radial direction of the blood vessel 71 is set in the x-direction, the direction in which the blood vessel 71 runs is set in the y-direction, and an irradiation position P11 is set at the origin is defined as an x-y orthogonal coordinate system.

As described above, in the present embodiment, a light-emitting element 52 that is situated over the blood vessel 71 to be measured is selected and used as the irradiation position P11, and measuring light is irradiated therefrom. Measuring light B irradiated from this irradiation position P11 is partly reflected by the skin surface 811 and partly enters the subcutaneous tissue layer 81. The measuring light entering the subcutaneous tissue layer 81 is transmitted through the subcutaneous tissue layer 81 while being complexly scattered therein and reaches the skin surface 811, as indicated by dashed arrows in FIGS. 5 and 6. Transmitted light that has thus reached the skin surface 811 includes light transmitted through the blood vessel 71, that is, light (blood-vessel transmitted light) whose path from the irradiation position P11 to the skin surface 811 passes through the blood vessel 71, and light that has not been transmitted through the blood vessel 71, that is, light (blood-vessel non-transmitted light) whose path from the irradiation position P11 to the skin surface 811 does not pass through the blood vessel 71.

Here, when the extent to which a blood-vessel transmitted light component is contained in transmitted light that is received by those light-receiving elements 54 that have the same distance (hereinafter referred to as "measurement point distance") from the irradiation position P11 and are situated on the same concentric circle is considered, it can be supposed that the proportion of the blood-vessel transmitted light component contained in the intensity of the transmitted light that is received at a position (hereinafter referred to as "first light-receiving position") P21 of the light-receiving element 54 that is situated over the blood vessel 71 and is separated from the irradiation position P11 in the y-direction is larger than that at other positions. This is because the transmitted light that is received at this first light-receiving position P21 is the light starting from the irradiation position P11 and propagating generally in the direction (y-direction) in which the blood vessel 71 runs. In contrast, transmitted light that is received at a position (hereinafter referred to as "second light-receiving position") P23 of the light-receiving element 54 that is separated from the irradiation position P11 in the x-direction and is not situated over the blood vessel 71 is the light starting from the irradiation position P11 and propagating generally in the radial direction (x-direction) of the blood vessel 71, and therefore it can be considered that the proportion of the blood-vessel transmitted light component is small.

Thus, the intensity distribution of the blood-vessel transmitted light and the intensity distribution of the transmitted light that are observed in the entire region of the skin surface 811 in the case where light (near-infrared light) similar to the measuring light that is used in actual measurement is irradiated from the irradiation position P11 were experimentally obtained. The experiment can be performed by reproducing the structure of the subcutaneous tissue layer 81 shown in FIGS. 5 and 6 by sample measurement in which a phantom that simulates a living body is used or by simulation that simulates a living body, and predicting the paths of light from the irradiation position. At this time, in order to clearly determine whether or not light is transmitted through the blood vessel 71, the experiment is performed by setting the blood vessel 71 as a fluorescent substance that is excited by a particular wavelength, an absorber having different absorption characteristics than the non-blood-vessel portions, or the like so that the determination can be made spectroscopically.

For example, an experiment was performed by reproducing the structure of the subcutaneous tissue layer 81 by a Monte Carlo simulation. At that time, a scatterer having an anisotropic parameter of 0.81, an index of refraction of 1.37, and a mean free path of 0.057 mm with respect to incident light was defined to simulate the subcutaneous tissue layer 81. Also, within the scatterer, a 2.3 mm diameter cylindrical structure that simulates the blood vessel 71 was set such that the center of the cylindrical structure is located at a depth of 2 mm from an upper surface of the scatterer. The simulation was performed 1,000,000 times.

Figure 7:
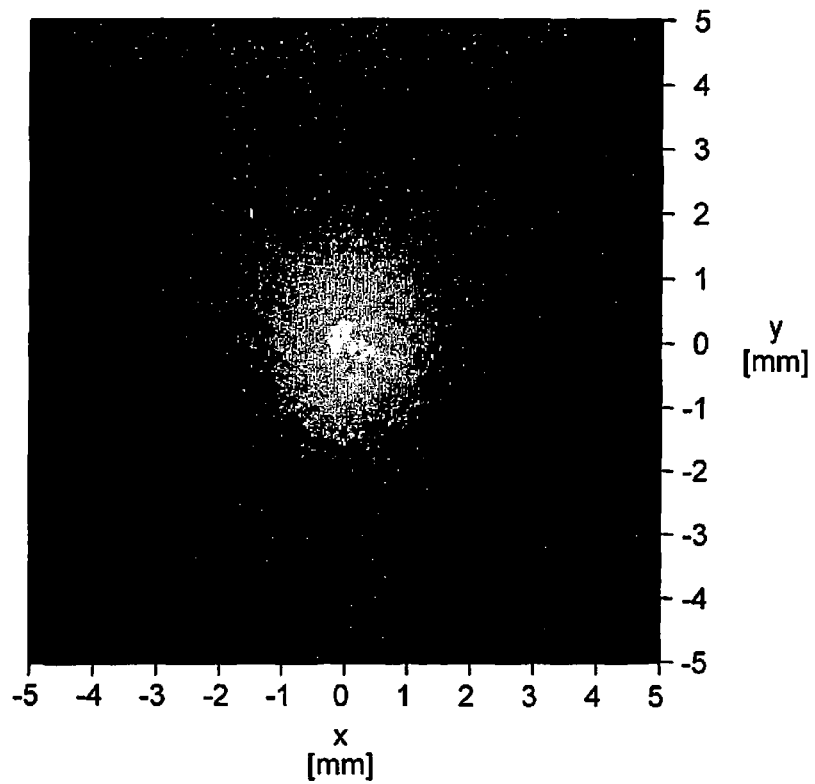
FIG. 7 shows a simulation result of intensity distribution of blood-vessel transmitted light obtained by reproducing the structure of the subcutaneous tissue layer.
Figure 8:
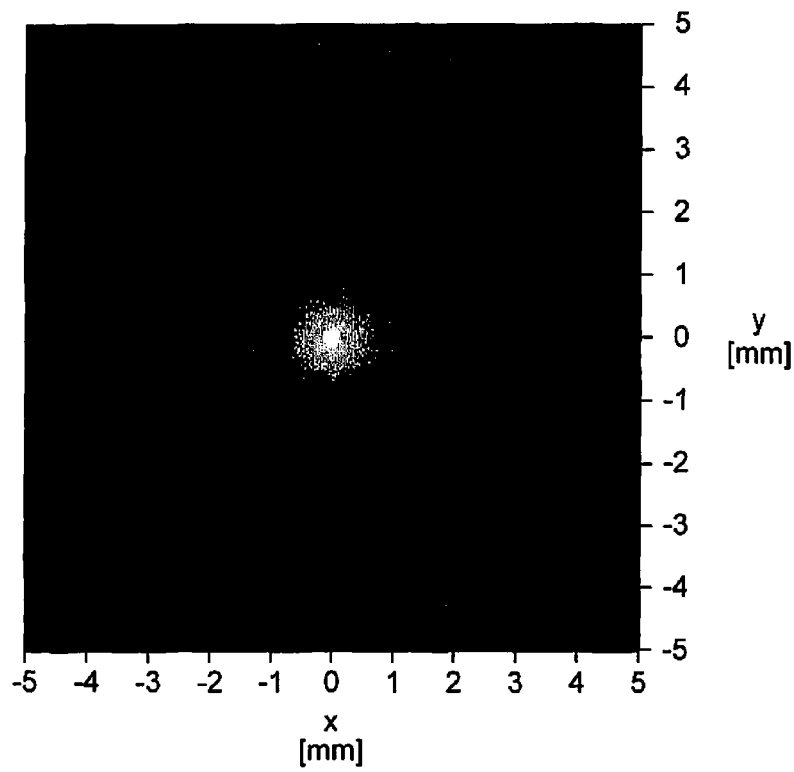
FIG. 8 shows a simulation result of intensity distribution of total transmitted light obtained by reproducing the structure of the subcutaneous tissue layer.
Figure 9:
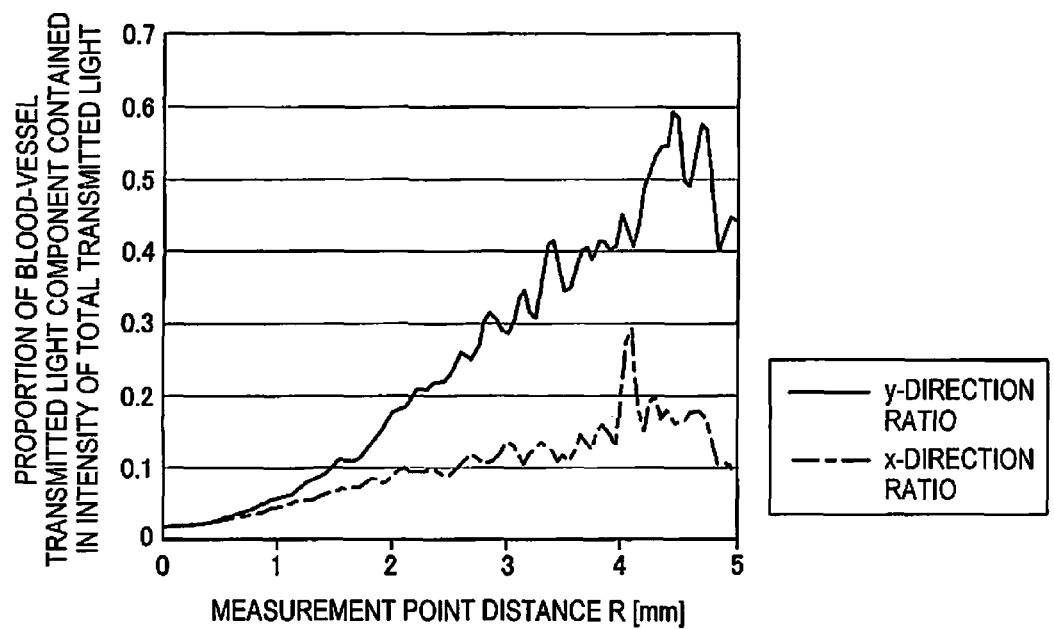
FIG. 9 graphically shows changes in y-direction ratio and x-direction ratio.

FIGS. 7 and 8 show the simulation result. FIG. 7 shows the intensity distribution of the blood-vessel transmitted light within the skin surface 811, and FIG. 8 shows the intensity distribution of the total transmitted light containing the blood-vessel transmitted light and the blood-vessel non-transmitted light within the skin surface 811. In FIGS. 7 and 8, the center corresponds to the origin of the x-y orthogonal coordinate system, that is, the irradiation position. Also, with respect to the observation results obtained at positions on the x-axis and the y-axis, the proportion of the blood-vessel transmitted light component contained in the intensity of the total transmitted light was obtained. FIG. 9 is a graph in which the horizontal axis indicates the measurement point distance R and the vertical axis indicates the proportion of the blood-vessel transmitted light component contained in the intensity of the total transmitted light, and in this graph, changes in the proportion (first proportion; hereinafter referred to as "y-direction ratio") of the blood-vessel transmitted light component on the y-axis are shown graphically by the solid line, and changes in the proportion (second proportion; hereinafter referred to as "x-direction ratio") of the blood-vessel transmitted light component on the x-axis are shown graphically by the alternate long and short dashed line.

As shown in FIG. 7, it was found that the bright region in which the intensity of the blood-vessel transmitted light is strong is wider in the y-direction than in the x-direction and the intensity of the blood-vessel transmitted light is distributed in an elliptical shape centered on the irradiation position and having its major axis set in the direction in which the blood vessel runs. In addition, when attention is paid to a position on the x-axis and a corresponding position on the y-axis, the y-direction ratio is higher than the x-direction ratio as shown in FIG. 9, and it was found that, at each positions on the y-axis, the total transmitted light contains a large amount of blood-vessel transmitted light. On the other hand, as shown in FIG. 8, it was found that the intensity of the total transmitted light is isotropically distributed around the irradiation position serving as the center.

Also, as shown in FIG. 9, both the y-direction ratio and the x-direction ratio tend to increase with the measurement point distance R until the measurement point distance R reaches a predetermined distance, and it was found that the content of the blood-vessel transmitted light in the total transmitted light is greater when the irradiation position and the light-receiving position are separated from each other to a certain extent. The reason for this is that the blood vessel 71 to be measured is present in a deep part, and thus the blood-vessel transmitted light conforms to the intensity distribution of light that is transmitted through a deep part of the subcutaneous tissue layer 81. Generally, when light irradiated onto a scatterer is observed on an irradiated surface side, light that is observed in the vicinity of the irradiation position contains much light reflected by a surface layer of the scatterer, and light that is observed at a position away from the irradiation position contains much light transmitted through a deep part of the scatterer. However, the intensity itself of the total transmitted light that is received decreases as the measurement point distance R increases.

Figure 10:
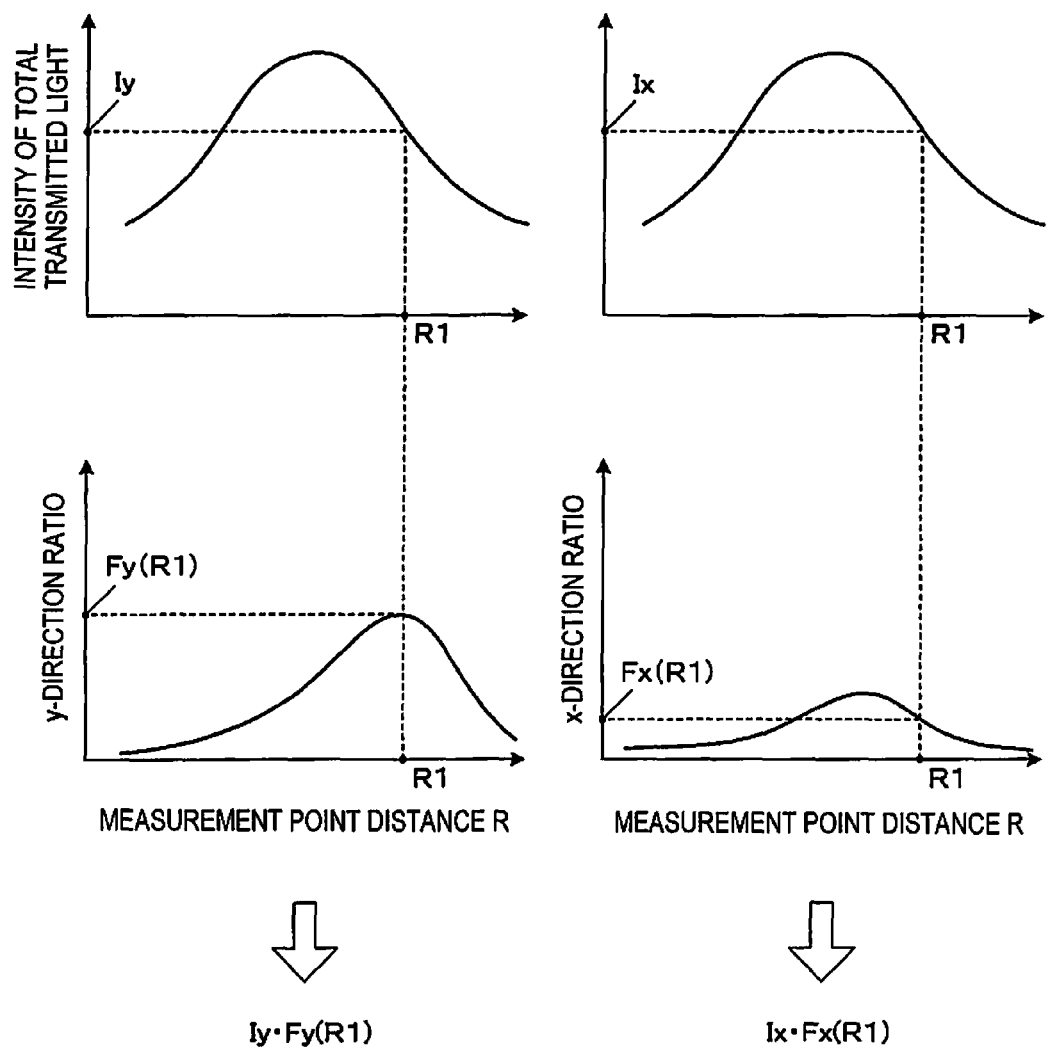
FIG. 10 is a conceptual diagram illustrating a synthesis process.

In view of the above-described simulation results, in the synthesis process of the present embodiment, a first light-reception result at the first light-receiving position P21, that is, the intensity of the total transmitted light received at the first light-receiving position P21, and a second light-reception result at the second light-receiving position P23 (the intensity of the total transmitted light received at the second light-receiving position P23) are synthesized using the y-direction ratio and the x-direction ratio that are obtained by simulation or the like in the above-described manner. FIG. 10 is a conceptual diagram illustrating the synthesis process. On the left-hand side in FIG. 10, the intensity distribution of total transmitted light on the y-axis is schematically shown in the upper graph, and changes in the y-direction ratio are schematically shown in the lower graph. On the other hand, on the right-hand side in FIG. 10, the intensity distribution of total transmitted light on the x-axis is schematically shown in the upper graph, and changes in the x-direction ratio are schematically shown in the lower graph.

To begin with, while the intensity of the total transmitted light is isotropically distributed relative to the irradiation position, the amount of the blood-vessel transmitted light component therein is larger at positions on the y-axis, and therefore, at a position on the y-axis that is determined by a measurement point distance (hereinafter referred to as "optimum measurement point distance") R1 at which the y-direction ratio is largest, the amount of the blood-vessel transmitted light component contained in the intensity of the total transmitted light is largest.

Thus, in the present embodiment, changes in the y-direction ratio are obtained, and a measurement point distance R corresponding to the largest value (hereinafter referred to as "applied y-direction ratio") of the y-direction ratio is set as the optimum measurement point distance R1 beforehand, which is then used in the synthesis process. For example, a y-direction ratio function that describes changes in the y-direction ratio in the lower graph on the left-hand side in FIG. 10 is obtained as a function Fy(R) of the measurement point distance R, and the optimum measurement point distance R1 and the applied y-direction ratio Fy(R1), which is a function value with respect to the optimum measurement point distance R1, are set in advance. This applied y-direction ratio Fy(R1) and an intensity Iy of total transmitted light that is received at the optimum measurement point distance R1 are multiplied together, and the obtained value Fy(R1)·Iy corresponds to the amount of blood-vessel transmitted light component (first amount of blood-vessel transmitted light component) contained in an intensity Iy of the total transmitted light. Thus, the blood-vessel transmitted light component can be extracted from the first light-reception result.

Then, in actual measurement, a light-receiving element 54 at the optimum measurement point distance R1 from the light-emitting element 52 serving as the irradiation position in the y-direction is selected to determine the first light-receiving position P21, and irradiation with measuring light and measurement of received light are performed. After that, in accordance with an equation (1) below, the first amount L of blood-vessel transmitted light component is calculated from the light-reception result (intensity of total transmitted light) $Iy_m$ at the first light-receiving position P21 and the applied y-direction ratio Fy(R1):

$$L = Fy(R1) \cdot Iy_m \quad (1)$$

On the other hand, the second light-reception result is used to reduce the effect of the transmitted light of the non-blood-vessel portions on the blood-vessel light absorption spectrum. As described above, the blood vessel is present in a deep part of the subcutaneous tissue layer, and therefore the blood-vessel transmitted light inevitably passes through a non-blood-vessel portion in the process until being received at the light-receiving position. In particular, since the interstitial fluid forming the non-blood-vessel portions contains glucose, which is an analysis target of the present blood component analyzing apparatus 10, there is a risk that the transmitted light of the non-blood-vessel portions may have an effect on the blood-vessel light absorption spectrum and lead to a decrease in the accuracy of calculation of the blood sugar level.

Here, total transmitted light that is observed at a position on the x-axis at an equal measurement point distance R also contains blood-vessel transmitted light, and the x-direction ratio is smaller than the y-direction ratio (see FIG. 9). For this reason, if the amount of blood-vessel transmitted light component contained in the intensity of the total transmitted light that is observed on the x-axis is obtained, and the difference between this amount and the first amount of blood-vessel transmitted light component is obtained, it is possible to obtain a relative value corresponding to the absorbance of the blood-vessel light absorption spectrum that is originally desired to be obtained. This is because although the amount of blood-vessel transmitted light component is reduced by using the difference, an effect of eliminating (cancelling) a light component that is transmitted through the non-blood-vessel portions can be expected.

Thus, in the synthesis process of the present embodiment, the blood-vessel transmitted light component is extracted from the second light-reception result in the same manner as the first blood-vessel transmitted light component. Specifically, changes in the x-direction ratio are obtained beforehand, and the x-direction ratio (hereinafter referred to as "applied x-direction ratio") at the optimum measurement point distance R1 is used in the synthesis process. For example, an x-direction ratio function describing changes in the x-direction ratio in the lower graph on the right-hand side in FIG. 10 is obtained as a function Fx(R) of the measurement point distance R, and the applied x-direction ratio Fx(R1) is set in advance. This applied x-direction ratio Fx(R1) and an intensity Ix of the total transmitted light at the optimum measurement point distance R1 are multiplied together, and the obtained value Fx(R1)·Ix corresponds to the amount of blood-vessel transmitted light component (second amount of blood-vessel transmitted light component) contained in the intensity Ix of the total transmitted light.

Then, in actual measurement, a light-receiving element 54 at the optimum measurement point distance R1 from the light-emitting element 52 serving as the irradiation position in the x-direction is selected to determine the second light-receiving position P23, and irradiation with measuring light and measurement of received light are performed. After that, in accordance with an equation (2) below, the second amount S of blood-vessel transmitted light component is calculated from the light-reception result (intensity of total transmitted light) $Ix_m$ at the second light-receiving position P23 and the applied x-direction ratio Fx(R1):

$$S = Fx_m(R1) \cdot Ix_m \quad (2)$$

After that, in accordance with an equation (3) below, a relative value I is calculated by subtracting the second amount of blood-vessel transmitted light component from the first amount of blood-vessel transmitted light component:

$$I = L - S \quad (3)$$

Figure 11:
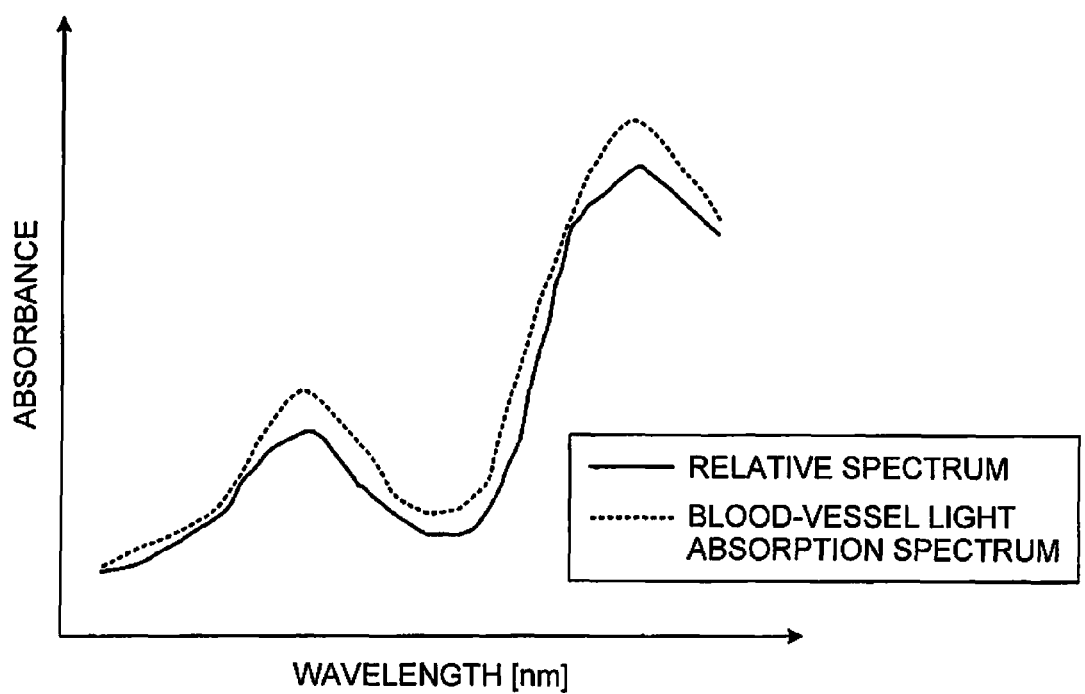
FIG. 11 schematically shows a result of synthesizing a relative spectrum.

Note that the measurement of received light is performed while shifting, for example, the center wavelength of the spectroscopic layer 55 by a unit wavelength at each time within a predetermined measurement wavelength range. Alternatively, the measurement of received light is performed while allowing the light-emitting elements 52 of the light-emitting layer 57 to emit light with a light-emitting wavelength that is shifted by a unit wavelength at each time. Then, relative values are obtained by performing the above-described synthesis process for each wavelength, and thus a relative spectrum is synthesized. FIG. 11 schematically shows a result of synthesizing a relative spectrum, and also shows a blood-vessel light absorption spectrum that is obtained by simulation or the like. As shown in FIG. 11, the relative spectrum is generally proportional to changes in absorbance depending on the wavelength that are indicated by the blood-vessel light absorption spectrum, and the expected effect of eliminating the light component transmitted through the non-blood-vessel portions is achieved. Accordingly, a blood component such as blood sugar in the blood can be accurately analyzed by performing data processing of the relative spectrum as appropriate.

Note that the higher the accuracy of approximation of the y-direction ratio by the y-direction ratio function Fy(R) and the accuracy of approximation of the x-direction ratio by the x-direction ratio function Fx(R), the higher the accuracies with which the blood-vessel transmitted light component can be extracted from the first light-reception result and the second light-reception result. Accordingly, when obtaining the y-direction ratio function Fy(R) and the x-direction ratio function Fx(R), simulation or the like is performed after precisely reproducing the subcutaneous fat layer by taking a measurement part and the like into account. Moreover, simulation is repeated a sufficient number of times for approximation of the y-direction ratio and the x-direction ratio, and then the y-direction ratio function Fy(R) and the x-direction ratio function Fx(R) are obtained.

Moreover, in some cases, it is also possible to perform blood measurement by taking a blood sample and create a database of the measurement result in advance, and then obtain the y-direction ratio function Fy(R) and the x-direction ratio function Fx(R) that are individualized to the subject 2 by using this database. This can reduce an error that is caused by individual differences of living bodies. In the case where the error due to individual differences would have a significant effect if a y-direction ratio function Fy(R) and an x-direction ratio function Fx(R) that are obtained by, for example, simulating scattering of a living body are used for general purposes, for example, in the case where the concentration of a trace substance in the blood is to be analyzed, it is desirable to set the y-direction ratio function Fy(R) and the x-direction ratio function Fx(R) for each subject 2.

Functional Configuration

Figure 12:
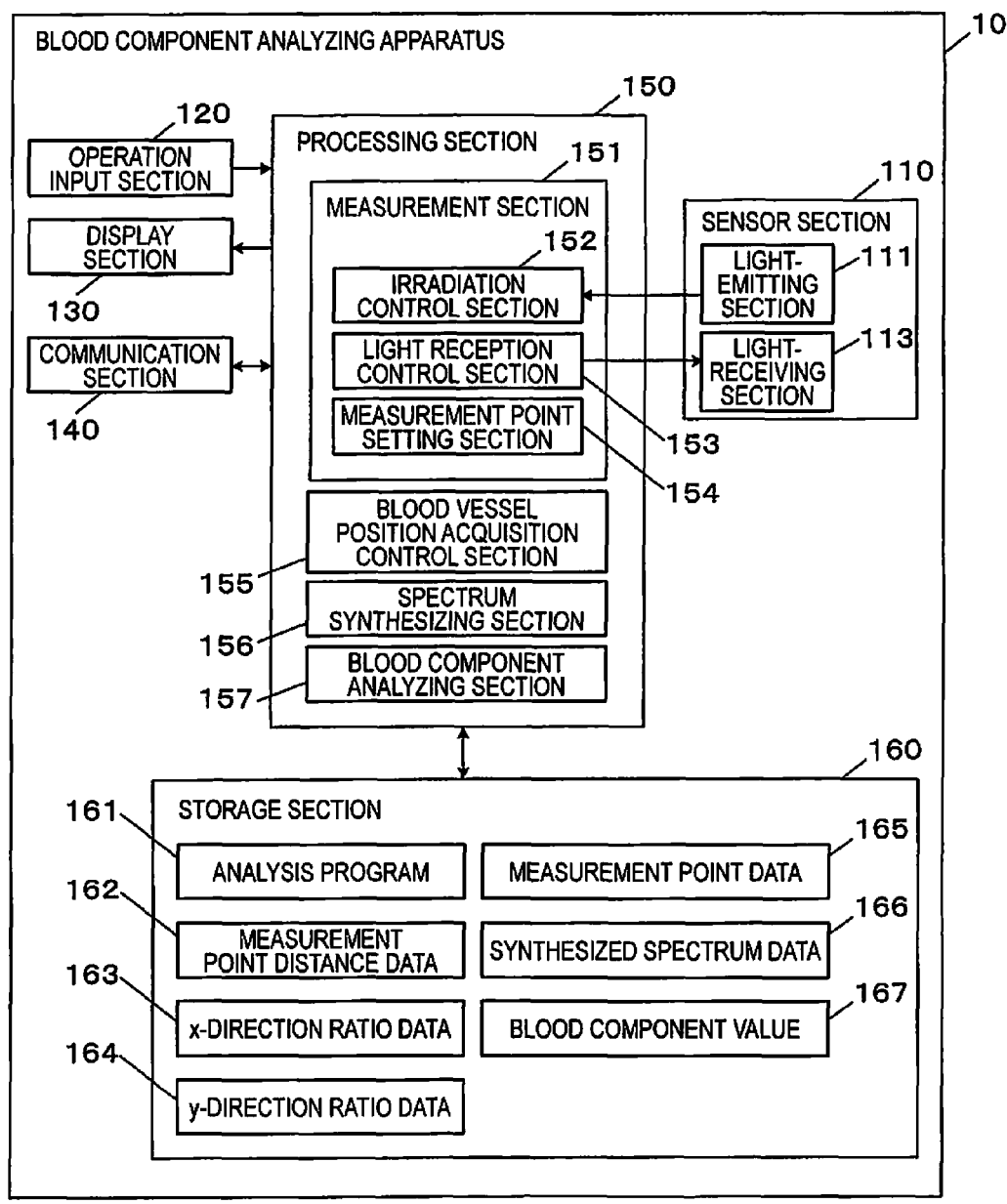
FIG. 12 is a block diagram showing a configuration example with respect to main functions of the blood component analyzing apparatus.

FIG. 12 is a block diagram showing a configuration example with respect to main functions of the blood component analyzing apparatus 10. As shown in FIG. 12, the blood component analyzing apparatus 10 includes a sensor section 110, an operation input section 120, a display section 130, a communication section 140, a processing section 150, and a storage section 160.

The sensor section 110 corresponds to the sensor module 50 in FIG. 2, and has a light-emitting section 111 configured by the plurality of light-emitting elements 52 and a light-receiving section 113 configured by the plurality of light-receiving elements 54.

The operation input section 120 is realized by various switches such as a button switch and a dial switch as well as an input device such as a touch panel, and outputs operation input signals to the processing section 150 in response to various types of operation input from the user. The operation switch 16 and the touch panel 18 in FIG. 1 correspond to this operation input section 120.

The display section 130 is realized by a display device such as an LCD (liquid crystal display) or an EL display (electroluminescence display), and displays various types of screens based on display signals input from the processing section 150. The touch panel 18 in FIG. 1 corresponds to this display section 130.

The communication section 140 is a communication device for transmitting and receiving information that is used inside the apparatus to and from external information processing equipment under the control of the processing section 150. The communication device 20 in FIG. 1 corresponds to this communication section 140. With regard to the communication system of the communication section 140, various types of systems such as a mode in which a wired connection is established via a cable that is in conformity with a predetermined communication standard, a mode in which a connection is established via an intermediate device that is called "cradle" and that doubles as a charger, and a mode in which a wireless connection is established using wireless communication are applicable.

The processing section 150 is realized by a control unit and an arithmetic unit, such as a microprocessor, such as a CPU (central processing unit) and a DSP (digital signal processor), and an ASIC (application specific integrated circuit), and performs integrated control of various sections of the blood component analyzing apparatus 10. The control board 30 in FIG. 1 corresponds to this processing section 150. The processing section 150 includes a measurement section 151, a blood vessel position acquisition control section 155, a spectrum synthesizing section 156 serving as a synthesis section, and a blood component analyzing section 157 serving as an analysis section. Note that those sections constituting the processing section 150 may be configured by hardware such as a dedicated module circuit.

The measurement section 151 performs irradiation with measuring light and measurement of received light. The measurement section 151 includes an irradiation control section 152, a light reception control section 153, and a measurement point setting section 154. The irradiation control section 152 controls light emission of each light-emitting element 52, which constitutes the light-emitting section 111, individually, and can be realized by using, for example, a so-called active matrix drive control technology. The light reception control section 153 performs control to read out an electric signal from total transmitted light received by each light-receiving element 54 of the light-receiving section 113, the electric signal corresponding to the intensity of the received total transmitted light.

The measurement point setting section 154 determines the irradiation position by selecting a light-emitting element 52 that is situated over the blood vessel to be measured. Moreover, the measurement point setting section 154 selects, based on the optimum measurement point distance R1 that is set by performing simulation or the like beforehand, light-receiving elements 54 so that the irradiation position, the first light-receiving position, and the second light-receiving position have a predetermined positional relationship. In the present embodiment, the measurement point setting section 154 determines the first light-receiving position by selecting a light-receiving element 54 that is situated at the optimum measurement point distance R1 from the irradiation position in the direction (y-direction) in which the blood vessel to be measured runs. Also, the second light-receiving position is determined by selecting a light-receiving element 54 that is situated at the optimum measurement point distance R1 from the irradiation position in the radial direction (x-direction) of the blood vessel to be measured, the radial direction being orthogonal to the y-direction. If no light-receiving element 54 is present at the optimum measurement point distance R1 from the irradiation position in each direction, the nearest light-receiving element 54 to the position at this optimum measurement point distance R1 can be selected.

The blood vessel position acquisition control section 155 acquires a biological image (see FIG. 4) under the skin that is covered by the sensor module 50 and performs image processing of the biological image, thereby acquiring the position of a blood vessel. In the present embodiment, this is realized by using a biological image capturing technique of a known vein authentication technology or the like or a technique for specifying a vein pattern from the biological image of a known vein authentication technology or the like as appropriate.

The spectrum synthesizing section 156, under the control of the irradiation control section 152 and the light reception control section 153, irradiates measuring light from the light-emitting element 52 that is selected as the irradiation position and measures the light received by the light-receiving elements 54 that are respectively selected as the first light-receiving position and the second light-receiving position, thereby obtaining the first light-reception result and the second light-reception result, and then synthesizes the first and second light-reception results using the applied y-direction ratio Fy(R1) and the applied x-direction ratio Fx(R1).

The blood component analyzing section 157 calculates the concentration of a predetermined target component in the blood based on a relative spectrum that is obtained as a result of the synthesis process. In the present embodiment, blood sugar level is calculated from the relative spectrum using an analysis method such as a multiple regression analysis method, a main component regression analysis method, a PLS regression analysis method, or an independent component analysis method.

The storage section 160 is realized by storage media such as various types of IC (integrated circuit) memories, such as a ROM (read-only memory), a flash ROM, and a RAM (random access memory), and a hard disk. In the storage section 160, a program for operating the blood component analyzing apparatus 10 and realizing various functions of the blood component analyzing apparatus 10, data to be used during execution of this program, and the like are stored beforehand or stored temporarily each time processing is performed. In FIG. 1, the main memory 34 and the analysis data memory 36 that are mounted on the control board 30 as well as the memory card 22 correspond to this storage section 160.

An analysis program 161 for causing the processing section 150 to function as the measurement section 151, the blood vessel position acquisition control section 155, the spectrum synthesizing section 156, and the blood component analyzing section 157 and performing an analysis process (see FIG. 14) is stored in the storage section 160.

Also, measurement point distance data 162, x-direction ratio data 163, y-direction ratio data 164, measurement point data 165, synthesized spectrum data 166, and a blood component value 167 are stored in the storage section 160.

The measurement point distance data 162 stores the optimum measurement point distance R1 that is set by performing simulation or the like beforehand. The y-direction ratio data 164 stores the applied y-direction ratio Fy(R1) that is set by performing simulation or the like beforehand. The x-direction ratio data 163 stores the applied x-direction ratio Fx(R1) that is set by performing simulation or the like beforehand.

Figure 13:
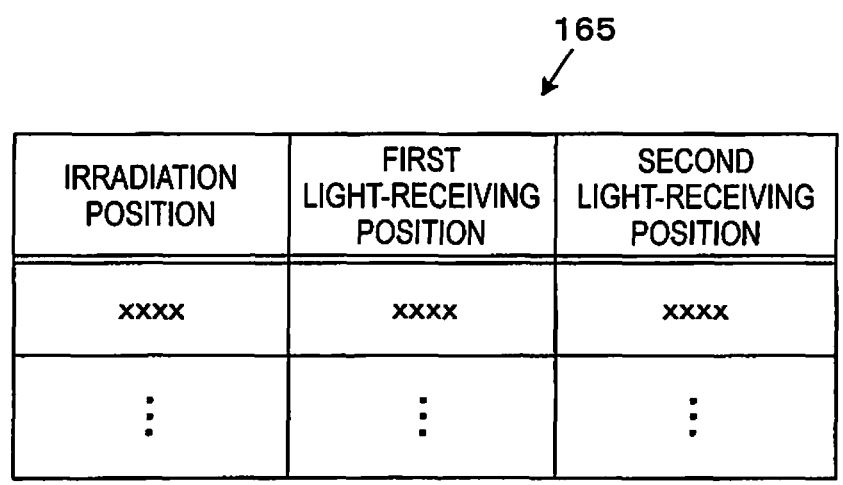
FIG. 13 shows an example of data configuration of measurement point data.

The measurement point data 165 stores the irradiation position, the first light-receiving position, and the second light-receiving position that are determined by the measurement point setting section 154. FIG. 13 shows an example of data configuration of the measurement point data 165. As shown in FIG. 13, the measurement point data 165 is a data table that stores the irradiation position, the first light-receiving position, and the second light-receiving position associated with one another. With respect to the irradiation position, identification numbers of relevant light-emitting elements 52 are registered, and with respect to the first light-receiving position and the second light-receiving position, identification numbers of respective relevant light-receiving elements 54 are registered. In the case where a plurality of positions over the blood vessel to be measured are used as irradiation positions, a first light-receiving position and a second light-receiving position are associated and set with respect to each irradiation position.

The synthesized spectrum data 166 stores data on a relative spectrum (see FIG. 11) that is synthesized by the spectrum synthesizing section 156. The blood component value 167 stores blood sugar level that is calculated by the blood component analyzing section 157.

Processing Flow

Figure 14:
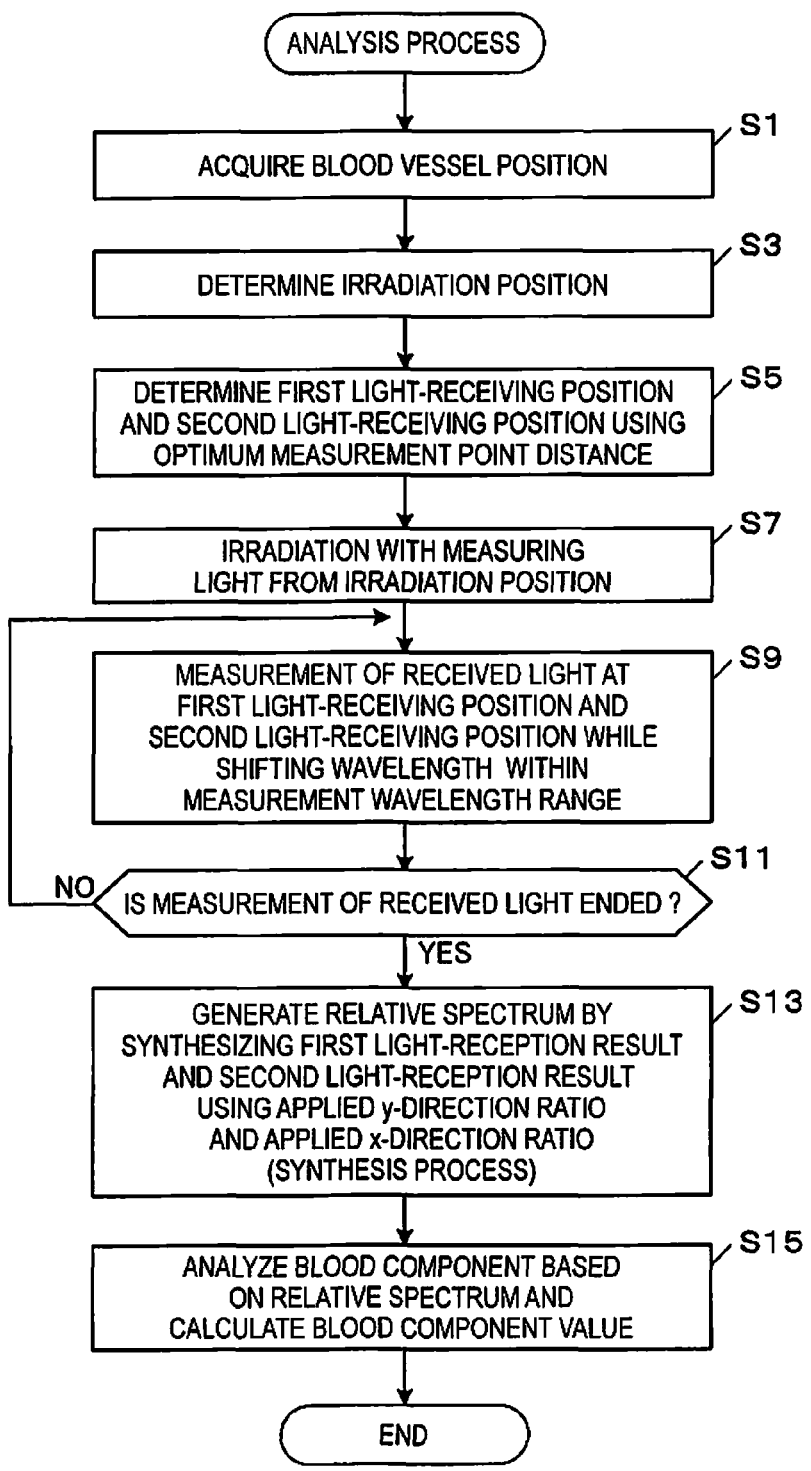
FIG. 14 is a flowchart illustrating a processing procedure of an analysis process.

FIG. 14 is a flowchart illustrating a processing procedure of the analysis process. Note that the processing described herein can be realized by the processing section 150 reading the analysis program 161 from the storage section 160 and executing this program. The blood component analyzing apparatus 10 carries out the blood component analyzing method by performing processing in accordance with the processing procedure in FIG. 14. This analysis process is started when the blood component analyzing apparatus 10 is attached to the body of the subject 2 and a predetermined analysis starting operation is input.

As shown in FIG. 14, in the analysis process, first, the blood vessel position acquisition control section 155 acquires the position of a blood vessel and selects the blood vessel to be measured (step S1). Prior to the processing in this step, the irradiation control section 152 causes all of the light-emitting elements 52 of the sensor module 50 to simultaneously emit light, and the light reception control section 153 performs measurement (capturing an image) of received light using all of the light-receiving elements 54. Then, the blood vessel position acquisition control section 155 performs, for each pixel of the obtained biological image (luminance image), comparison with a reference luminance, binarization, and filtering, and thus acquires the position of a blood vessel. A pixel having a luminance that is less than the reference luminance indicates the blood vessel, and a pixel having a luminance that is equal to or more than the reference luminance indicates a non-blood-vessel region.

Subsequently, the measurement point setting section 154 determines the irradiation position by selecting a light-emitting element 52 that is situated over the blood vessel (step S3). Also, the measurement point setting section 154 determines, in accordance with the irradiation position that is determined in step S3, the first light-receiving position and the second light-receiving position by selecting light-receiving elements 54 using the optimum measurement point distance R1 (step S5). At this time, the measurement point setting section 154 creates the measurement point data 165 in which identification numbers of the light-emitting element 52 and the light-receiving elements 54 that are selected as the irradiation position, the first light-receiving position, and the second light-receiving position are registered.

After that, irradiation with measuring light and measurement of received light are performed. That is to say, first, the irradiation control section 152 controls light emission of the light-emitting element 52 that is registered as the irradiation position in the measurement point data 165, thereby irradiating the measuring light from the irradiation position (step S7). Then, the light reception control section 153 performs measurement of received light using the light-receiving elements 54 that are registered respectively as the first light-receiving position and the second light-receiving position in the measurement point data 165, while shifting the center wavelength of the spectroscopic layer 55 by a unit wavelength at each time within the measurement wavelength range (step S9). When measurement of received light with respect to all the wavelengths within a measurement wavelength range has been finished, measurement of received light is ended (step S11: YES).

Subsequently, the spectrum synthesizing section 156 synthesizes the first light-reception result and the second light-reception result that are obtained for each wavelength in step S9 (step S13). Specifically, the spectrum synthesizing section 156 multiplies the first light-reception result by the applied y-direction ratio Fy(R1) to calculate the first amount L of blood-vessel transmitted light component (equation (1) above), multiplies the second light-reception result by the applied x-direction ratio Fx(R1) to calculate the second amount S of blood-vessel transmitted light component (equation (2) above), and subtracts the second amount S of blood-vessel transmitted light component from the first amount L of blood-vessel transmitted light component to calculate the relative value I (equation (3) above). The spectrum synthesizing section 156 performs this processing for each wavelength, thereby synthesizing a relative spectrum.

After that, the blood component analyzing section 157 calculates blood sugar level based on the relative spectrum that is synthesized in step S13 and stores the calculated blood sugar level as the blood component value 167 (step S15), and thus this process is ended.

As described above, according to the present embodiment, it is possible to set the optimum measurement point distance R1, the applied y-direction ratio Fy(R1), and the applied x-direction ratio Fx(R1) beforehand by defining the direction in which a blood vessel runs as the y-direction and the radial direction of that blood vessel as the x-direction, the radial direction being orthogonal to the y-direction, and obtaining the y-direction ratio function Fy(R) and the x-direction ratio function Fx(R) by performing simulation or the like. Then, during actual measurement, it is possible to determine the irradiation position by selecting a light-emitting element 52 that is situated over the blood vessel, to determine the first light-receiving position by selecting a light-receiving element 54 that is situated over the blood vessel and that is at the optimum measurement point distance R1 from the irradiation position in the y-direction, and to determine the second light-receiving position by selecting a light-receiving element 54 that is not situated over the blood vessel and that is at the optimum measurement point distance R1 from the irradiation position in the x-direction. Then, it is possible to perform irradiation with measuring light from the irradiation position and measurement of received light.

With this configuration, it is possible to determine the first light-receiving position on the y-axis, on which the proportion of the blood-vessel transmitted light component contained in the intensity of the total transmitted light that is received is large, and to determine the second light-receiving position on the x-axis, on which the proportion of the blood-vessel transmitted light component is small. Moreover, since irradiation with measuring light and measurement of received light can be performed using selectively the light-emitting elements 52 and the light-receiving elements 54 that are provided in the sensor module 50, the effects of unwanted transmitted light and reflected light can be reduced when compared with a case where, for example, measurement (capturing an image) of received light is performed by causing all of the light-emitting elements 52 to simultaneously emit light.

Then, it is possible to synthesize a relative spectrum of the blood-vessel light absorption spectrum that reflects the amount of blood-vessel transmitted light component by extracting the blood-vessel transmitted light component from the first light-reception result for each wavelength to calculate the first amount of blood-vessel transmitted light component, extracting the blood-vessel transmitted light component from the second light-reception result for each wavelength to calculate the second amount of blood-vessel transmitted light component, and cancelling the blood-vessel non-transmitted light component by obtaining the difference between the first amount of blood-vessel transmitted light component and the second amount of blood-vessel transmitted light component. Therefore, the blood-vessel transmitted light component can be appropriately extracted from the intensity of the total transmitted light, and a blood component such as blood sugar can be accurately analyzed by using the extracted blood-vessel transmitted light component.

Note that in the above-described embodiment, the first light-receiving position is determined so as to be at a distance from the irradiation position in the direction (y-direction) in which the blood vessel runs, and the second light-receiving position is determined so as to be at a distance from the irradiation position in the radial direction (x-direction) of the blood vessel, the radial direction being orthogonal to the y-direction; however, it is only required that the first light-receiving position is a position that is situated over the blood vessel and is different from the irradiation position, and the second light-receiving position is a position that is not situated over the blood vessel. That is to say, the first light-receiving position and the second light-receiving position may be determined so as to have a positional relationship in which a direction containing the irradiation position and the first light-receiving position and a direction containing the irradiation position and the second light-receiving position intersect each other. In that case, the optimum measurement point distance R1, the applied y-direction ratio Fy(R1), and the applied x-direction ratio Fx(R1) are set beforehand by obtaining a y-direction ratio function Fy(R) and an x-direction ratio function Fx(R) that are respectively appropriate for the direction containing the irradiation position and the first light-receiving position and the direction containing the irradiation position and the second light-receiving position.

For example, in the case where the first light-receiving position and the second light-receiving position cannot be determined in mutually orthogonal directions due to the limitations of the apparatus such as the limitation by the configuration (arrangement of the light-emitting elements 52 and the light-receiving elements 54) of the sensor module 50, the first and second light receiving positions may be determined according to this modification.

Moreover, in the above-described embodiment, the optimum measurement point distance R1, the applied y-direction ratio Fy(R1), and the applied x-direction ratio Fx(R1) are set in advance and used in the synthesis process. Alternatively, these values may be set to be variable according to the depth of the blood vessel or the diameter of the blood vessel.

Here, the intensity distribution of blood-vessel transmitted light shown in FIG. 7 varies according to the depth of the blood vessel. Specifically, the deeper the depth of the blood vessel, the wider in the y-direction and the narrower in the x-direction the range in which the intensity of the blood-vessel transmitted light is strong (the longer the major axis and the shorter the minor axis of the ellipse of the intensity distribution). Moreover, the deeper the depth of the blood vessel, the smaller on the whole the proportion of the blood-vessel transmitted light contained in the intensity of the total transmitted light in both the y-direction and the x-direction, and also the larger the optimum measurement point distance R1, at which the y-direction ratio is largest, from the irradiation position. On the other hand, the intensity distribution of the blood-vessel transmitted light also varies according to the diameter of the blood vessel. In this case, the larger the diameter of the blood vessel, the wider the range in which the intensity of the blood-vessel transmitted light is strong in the x-direction (the longer the minor axis of the ellipse of the intensity distribution, and thus the closer the ellipse approximates to a circle). Also, the larger the diameter of the blood vessel, the larger on the whole the proportion of the blood-vessel transmitted light contained in the intensity of the total transmitted light in the x-direction.

Thus, the y-direction ratio function Fy(R) and the x-direction ratio function Fx(R) may also be obtained in advance by performing simulation or the like by reproducing subcutaneous tissue layers with varying blood vessel depths or subcutaneous tissue layers with varying blood vessel diameters, assuming a part of a living body or different blood vessels, for example. Then, the optimum measurement point distance R1, the applied y-direction ratio Fy(R1), and the applied x-direction ratio Fx(R1) may be prepared as an applied ratio data table that stores these values associated with each blood vessel depth and each blood vessel diameter.

FIG. 15 shows an example of data configuration of the applied ratio data table. As shown in FIG. 15, the applied ratio data table is a data table in which data sets $D_{11}$, $D_{12}$, ... of the optimum measurement point distance R1, the applied y-direction ratio Fy(R1), and the applied x-direction ratio Fx(R1) are set for respective combinations of value ranges $V_{11}$ to Vn, $V_{12}$ to Vn, ... of the blood vessel depth and value ranges $V_{21}$ to $V_{22}$, $V_{22}$ to $V_{23}$, ... of the blood vessel diameter. The data set of R1, Fy(R1), and Fx(R1) for each combination of the blood vessel depth and the blood vessel diameter is set beforehand by reproducing a subcutaneous tissue layer corresponding to that combination and thereby individually obtaining the y-direction ratio function Fy(R) and the x-direction ratio function Fx(R).

Then, in actual measurement, the optimum measurement point distance R1, the applied y-direction ratio Fy(R1), and the applied x-direction ratio Fx(R1) corresponding to the depth and the diameter of the blood vessel to be measured are read out from the applied ratio data table and used. The depth of a blood vessel can be determined by performing image processing of a biological image that is acquired in order to select the blood vessel to be measured and discriminating the sharpness and the contrast of a boundary portion of the blood vessel in the biological image. The diameter of a blood vessel can be determined by calculating the width of the blood vessel in the biological image in the radial direction.

According to this modification, when attention is focused on the depth of the blood vessel, it is possible to set the values such that the deeper the depth of the blood vessel, the larger the y-direction ratio relative to the x-direction ratio. In addition to this, it is possible to set the optimum measurement point distance R1 such that the deeper the depth of the blood vessel, the larger the optimum measurement point distance R1. Moreover, when attention is focused on the diameter of the blood vessel, it is possible to set the values such that the larger the diameter of the blood vessel, the larger the x-direction ratio relative to the y-direction ratio. In this manner, a relative spectrum of the blood-vessel light absorption spectrum that reflects the amount of blood-vessel transmitted light component even more can be obtained.

Moreover, in the above-described embodiment, the case where the blood-vessel transmitted light component is extracted from the intensity of the total transmitted light to synthesize the relative spectrum of the blood-vessel light absorption spectrum has been described. Alternatively, it is also possible to extract light (blood-vessel non-transmitted light) that is not transmitted through the blood vessel from the intensity of the total transmitted light and synthesize a relative spectrum of a spectroscopic spectrum (non-blood-vessel portion light absorption spectrum) of the blood-vessel non-transmitted light. In this case, a y-direction ratio function and an x-direction ratio function with respect to the blood-vessel non-transmitted light are obtained beforehand. For example, the y-direction ratio function and the x-direction ratio function can be obtained by obtaining the reciprocals of the y-direction ratio function Fy(R) and the x-direction ratio function Fx(R) described in the above embodiment.

According to this modification, a relative spectrum of the non-blood-vessel portion light absorption spectrum that does not reflect the amount of blood-vessel transmitted light component can be synthesized, and this makes it possible to obtain the concentration of a substance that is present in a non-blood-vessel portion, for example, the concentration of glucose in the interstitial fluid.

Moreover, in the above-described embodiment, measurement of received light is performed at two light-receiving positions, namely, the first light-receiving position and the second light-receiving position, with respect to one irradiation position; however, a configuration may also be adopted in which measurement of received light is performed at three or more light-receiving positions. For example, it is possible to determine two light-receiving positions that are situated over the blood vessel and one light-receiving position that is not situated over the blood vessel and perform measurement of received light at these light-receiving positions.

By way of example, it is possible to select a light-receiving element 54 at the optimum measurement point distance R1 from the irradiation position P11 in a direction opposite to the first light-receiving position P21 shown in FIG. 5 and the like (negatively in the y-direction) and determine that light-receiving element 54 as a third light-receiving position to perform measurement of received light. The manner in which a third light-reception result at the third light-receiving position is used is not particularly limited, but, for example, in the synthesis process, processing for calculating a third amount of blood-vessel transmitted light component from the third light-reception result using the y-direction ratio is further performed. Then, it is possible to obtain an average value of the first amount of blood-vessel transmitted light component and the third amount of blood-vessel transmitted light component and calculate a relative value by subtracting the second amount of blood-vessel transmitted light component from the obtained average value.

The depth of the blood vessel to be measured is not necessarily uniform throughout the blood vessel in its running direction because, for example, the blood vessel may be inclined rather than being parallel to the skin surface. For this reason, the synthesis result may vary depending on which position over the blood vessel is determined as the irradiation position, and there is a risk that this may lead to a decrease in the accuracy of blood component analysis. According to this modification, it is possible to reduce such variation in the synthesis result and thereby improve the accuracy of blood component analysis.

Alternatively, it is also possible to perform simulation or the like by reproducing a subcutaneous tissue layer in which a blood vessel is inclined with respect to the skin surface as described above, obtain a y-direction ratio function for a third light-receiving position separately from the y-direction ratio function Fy(R) for the first light-receiving position beforehand, and individually set a y-direction ratio to be applied to the first light-receiving position and a y-direction ratio to be applied to the third light-receiving position. In this manner, a relative spectrum of the blood-vessel light absorption spectrum that reflects the amount of blood-vessel transmitted light component even more can be synthesized.

Moreover, in the above-described embodiment, a measurement point distance R at which the y-direction ratio is largest is used in the synthesis process as the optimum measurement point distance R1; however it is not necessarily required to use the largest value. In this case, a function value Fy(R1) of the y-direction ratio function Fy(R) corresponding to a measurement point distance R that is set as the optimum measurement point distance R1 can be used as the applied y-direction ratio. The same applies to the x-direction ratio.

Moreover, in the above-described embodiment, the case where a function value Fx(R1) of the x-direction ratio function Fx(R) at the optimum measurement point distance R1 at which the y-direction ratio is largest is used as the applied x-direction ratio has been described as an example. Alternatively, a configuration may also be adopted in which optimum measurement point distances R1 with respect to the y-direction and the x-direction are individually set. For example, with respect to the x-direction ratio, the applied x-direction ratio Fx(R1) may be set by, for example, using a measurement point distance R at which the value of the x-direction ratio is largest as the optimum measurement point distance R1 or by using a measurement point distance R at which the value of the x-direction ratio is smallest as the optimum measurement point distance R1. In this case, the first light-receiving position and the second light-receiving position are determined using the optimum measurement point distances R1 in the respective directions.

Moreover, in the above-described embodiment, the case where the blood component analyzing apparatus 1 measures blood sugar as the blood component has been mainly described; however, the present embodiment can of course be equally applied to cases where other blood components are measured. For example, the present embodiment can be applied to measurement of the level of an enzyme such as GPT (glutamic pyruvic transaminase), the level of a plasma protein such as albumin, the cholesterol value, the lactic acid level, and the like.

What is claimed is:

1. A blood component analyzing method, comprising:
   setting a predetermined irradiation position, a first light-receiving position, and a second light-receiving position such that the predetermined irradiation position and the first light-receiving position are different from each other and situated over a blood vessel, the second light-receiving position is not situated over the blood vessel, and a first axis connecting the predetermined irradiation position and the first light-receiving position intersects with a second axis connecting the predetermined irradiation position and the second light-receiving position:
   operating a light source positioned at the predetermined irradiation position to irradiate measuring light to the blood vessel from the predetermined irradiation position at a predetermined time;
   operating a first photodetector positioned at the first light-receiving position to receive light, which has been irradiated from the predetermined irradiation position at the predetermined time and has passed through the blood vessel, at the first light-receiving position;
   operating a second photodetector positioned at the second light-receiving position to receive light, which has been irradiated from the predetermined irradiation position at the predetermined time and has passed through the blood vessel, at the second light-receiving position;
   synthesizing a first light-reception result at the first light-receiving position and a second light-reception result at the second light-receiving position by performing a predetermined synthesis process based on a positional relationship among the irradiation position, the first light-receiving position, and the second light-receiving position; and
   analyzing a blood component using a result of the synthesis.

2. The blood component analyzing method according to claim 1,
   wherein the synthesis includes:
   setting a first proportion of a blood-vessel transmitted light component contained in the first light-reception result and a second proportion of an amount of the blood-vessel transmitted light component contained in the second light-reception result; and
   performing the predetermined synthesis process using the first proportion and the second proportion.

3. The blood component analyzing method according to claim 2,
   wherein performing the predetermined synthesis process includes calculating a difference between an amount (hereinafter referred to as "first amount of blood-vessel transmitted light component") of the blood-vessel transmitted light component contained in the first light-reception result, the amount being calculated using the first proportion, and an amount (hereinafter referred to as "second amount of blood-vessel transmitted light component") of the blood-vessel transmitted light component contained in the second light-reception result, the amount being calculated using the second proportion.

4. The blood component analyzing method according to claim 2,
   wherein setting the first proportion includes setting the first proportion at a proportion corresponding to a distance between the irradiation position and the first light-receiving position, and
   setting the second proportion includes setting the second proportion at a proportion corresponding to a distance between the irradiation position and the second light-receiving position.

5. The blood component analyzing method according to claim 2,
   wherein the first proportion and the second proportion are set to be variable according to a depth of the blood vessel.

6. The blood component analyzing method according to claim 2, further comprising:
   setting the first proportion and the second proportion such that, when compared with the first proportion relative to the second proportion when the blood vessel is at a first depth, the first proportion relative to the second proportion is larger when the blood vessel is at a second depth that is deeper than the first depth.

7. The blood component analyzing method according to claim 2, further comprising:
setting the first proportion and the second proportion to be variable according to a diameter of the blood vessel.

8. The blood component analyzing method according to claim 2, further comprising:
setting the first proportion and the second proportion such that, when compared with the second proportion relative to the first proportion when the blood vessel has a first diameter, the second proportion relative to the first proportion is larger when the blood vessel has a second diameter that is larger than the first diameter.

9. The blood component analyzing method according to claim 1, further comprising:
determining the first light-receiving position and the second light-receiving position by changing a distance from the irradiation position to the first light-receiving position and a distance from the irradiation position to the second light-receiving position according to a depth of the blood vessel.

10. The blood component analyzing method according to claim 1, further comprising:
determining the first light-receiving position and the second light-receiving position by changing a distance from the irradiation position to the first light-receiving position and a distance from the irradiation position to the second light-receiving position according to a diameter of the blood vessel.

11. The blood component analyzing method according to claim 1,
wherein the setting of the predetermined irradiation position, the first light-receiving position, and the second light-receiving position includes setting the predetermined irradiation position, the first light-receiving position, and the second light-receiving position such that the first light-receiving position and the second light-receiving position are positioned concentrically relative to the predetermined irradiation position.

12. The blood component analyzing method according to claim 1, wherein
the setting of the predetermined irradiation position, the first light-receiving position, and the second light-receiving position includes setting the predetermined irradiation position, the first light-receiving position, and the second light-receiving position such that the first axis is perpendicular to the second axis.

13. The blood component analyzing method according to claim 2, wherein
the setting of the first proportion and the second proportion includes setting the first proportion and the second proportion in advance before the operating of the light source to irradiate the measuring light.

14. A blood component analyzing apparatus comprising:
a measurement point setting section that sets a predetermined irradiation position, a first light-receiving position, and a second light-receiving position such that the predetermined irradiation position and the first light-receiving position are different from each other and are configured to be situated over a blood vessel, the second light-receiving position is configured not to be situated over the blood vessel, and a first axis connecting the predetermined irradiation position and the first light-receiving position intersects with a second axis connecting the predetermined irradiation position and the second light-receiving position;
a light source that is positioned at the predetermined irradiation position and irradiates measuring light to the blood vessel from the predetermined irradiation position at a predetermined time;
a first photodetector that is positioned at the first light-receiving position and receives light, which has been irradiated from the predetermined irradiation position at the predetermined time and has passed through the blood vessel, at the first light-receiving position;
a second photodetector that is positioned at the second light-receiving position and receives light, which has been irradiated from the predetermined irradiation position at the predetermined time and has passed through the blood vessel, at the second light-receiving position;
a synthesis section that synthesizes a first light-reception result at the first light-receiving position and a second light-reception result at the second light-receiving position by performing a predetermined synthesis process based on a positional relationship among the irradiation position, the first light-receiving position, and the second light-receiving position; and
an analysis section that analyzes a blood component using a result of the synthesis.

* * * * *